United States Patent [19]
Anderson et al.

[11] Patent Number: 5,464,019
[45] Date of Patent: Nov. 7, 1995

[54] AIRFLOW CONTROL MANIFOLD FOR AUTOMATIC BLOOD PRESSURE MONITORING DEVICE

[75] Inventors: R. Carver Anderson, Seattle; Glen Eaton, Sultan, both of Wash.

[73] Assignee: SpaceLabs, Inc., Redmond, Wash.

[21] Appl. No.: 929,188

[22] Filed: Aug. 11, 1992

[51] Int. Cl.⁶ ...................................................... A61B 5/00
[52] U.S. Cl. .......................... 128/677; 128/685; 128/680
[58] Field of Search ................................... 128/677–686; 137/625.65, 596.17, 883

[56] References Cited

U.S. PATENT DOCUMENTS

| | | | |
|---|---|---|---|
| 4,175,103 | 11/1979 | Stoltman | 137/625.65 |
| 4,378,807 | 4/1983 | Peterson | 128/680 |
| 4,549,550 | 10/1985 | Kami | 128/686 |
| 4,619,481 | 10/1986 | Grudzinskas | 137/883 |
| 4,706,684 | 11/1987 | Sorenson et al. | 128/686 |
| 4,718,428 | 1/1988 | Russell | 128/681 |
| 4,774,960 | 10/1988 | Arnold et al. | 128/681 |
| 4,858,616 | 8/1989 | Samaras et al. | 128/680 |
| 4,917,116 | 4/1990 | La Viola et al. | 128/681 |
| 4,944,331 | 7/1990 | Tackett | 137/625.62 |
| 5,285,791 | 2/1994 | Smith | 128/680 |

*Primary Examiner*—Lee S. Cohen
*Assistant Examiner*—Robert L. Nasser, Jr.
*Attorney, Agent, or Firm*—Seed and Berry

[57] ABSTRACT

A blood pressure monitoring device utilizing an integrally formed, substantially unitary manifold is shown and described. The manifold has an air inlet port for communicating with an air pump, and two cuff ports, one to be coupled to a blood pressure cuff, the other to be used to sample ambient pressure. The manifold further includes a transducer port for communicating with a pressure transducer and four valve seats, for receiving high- and low-pressure distribution valves, and high- and low-pressure relief valves. The distribution valves utilize solenoids, and therefore have two positions, namely, energized and de-energized. When the solenoids are energized, communication is allowed between a first plenum chamber and the cuff ports, the first plenum chamber also being in communication with the high-pressure relief valve and the air inlet port. Simultaneously, communication between the cuff ports and atmosphere is sealed off. In contrast, when the solenoids are in their de-energized position, communication between the first plenum chamber and the cuff ports is sealed off, allowing communication between the cuff ports and atmosphere. The manifold further includes a second plenum chamber that is in communication with a low-pressure relief valve and a second cuff port, and is selectively in communication with the first plenum chamber, the two plenum chambers being in communication when the low-pressure distribution valve is in an energized position.

17 Claims, 5 Drawing Sheets

5,464,019

AIRFLOW CONTROL MANIFOLD FOR AUTOMATIC BLOOD PRESSURE MONITORING DEVICE

TECHNICAL FIELD

This invention relates to blood pressure monitoring, and more particularly, to an integrally formed manifold that interacts with and connects the elements of an automatic blood pressure monitoring device.

BACKGROUND OF THE INVENTION

Blood pressure is normally measured by placing a blood pressure cuff around the arm of a patient over the brachial artery. The cuff typically includes an inflatable bladder placed in an outer casing. The bladder is inflated to compress the arm of the patient, thereby pinching off the flow of blood through the brachial artery. The pressure in the bladder is gradually reduced while listening for sounds caused by the flow of blood through the brachial artery and measuring the air pressure in the bladder. When blood flow is detected during systole, the air pressure in the bladder is recorded as the systolic blood pressure. Similarly, when blood flow is detected during diastole, the air pressure in the bladder is recorded as the diastolic blood pressure.

Although the most common device for measuring blood pressure using the above-described procedure is the familiar manually pumped cuff using a mercury manometer as the pressure measuring device, automated patient monitoring systems are also in common use.

One example of an instrument for automatically performing medical diagnostic tests is the ambulatory or bedside blood pressure monitor. These blood pressure monitors include a conventional blood pressure cuff connected through a tube to a monitoring instrument. The monitoring instrument includes an electric motor driving an air pump, a pressure traducer for measuring the air pressure in the cuff, and, if a separate transducer is not used, to also detect Korotkoff sounds or oscillometric pulses, which are generated by the flow of blood through the brachial artery. All of these components are generally controlled by a microprocessor. The monitoring instrument may also include a recording device, such as a magnetic tape recorder, or a digital display for providing a visual blood pressure indication.

In operation, the motor is energized to inflate the cuff while the pressure in the cuff is monitored by the pressure transducer. When the cuff pressure reaches a predetermined value, the processor periodically actuates an air valve to incrementally bleed air from the cuff thereby reducing the cuff pressure. At each cuff pressure value, the transducer measures the cuff pressure and detects Korotkoff sounds or oscillometric pulses. The processor, using a rather complex algorithm, then determines the blood pressure from a table of cuff pressures and data indicating whether Korotkoff sounds or oscillometric pulses are detected at each cuff pressure. The blood pressure is then either recorded or displayed.

Although automated blood pressure monitors of the type described above allow the blood pressure of a patient to be easily measured without the need for trained personnel, they have disadvantages. Most significantly perhaps, they utilize numerous tubes and connections, which results in the leakage of air from the system. This inadvertent leakage can adversely affect the accuracy of blood pressure measurements because the air pressure in the cuff will be changing while a measurement is being taken. Furthermore, the rate of leakage is not uniform, so the leakage cannot be compensated for by the monitor.

In addition, conventional automated blood pressure monitoring systems tend to be bulky and somewhat expensive, and to have several wear points. A need therefore exists for a blood pressure monitoring device that will lose a minimum of air through inadvertent leakage, and that will be compact and resist wear.

SUMMARY OF THE INVENTION

It is therefore an object of this invention to provide a blood pressure monitoring device wherein the leakage of air from the device is minimal, thereby increasing the accuracy of blood pressure measurements taken by the device.

It is another object of this invention to provide a blood pressure monitoring device that eliminates the need for numerous tubes and connections, thereby reducing the size and cost of the device.

It is another object of this invention to provide a blood pressure monitoring device wherein the structure of the device tends to resist wear, thereby extending the longevity of the device.

These and other objects of the invention, as will be apparent herein, are accomplished by providing a blood pressure monitoring device that consists of an integrally formed manifold which structurally and pneumatically interacts with and connects an air pump, a blood pressure cuff and a transducer. The manifold is a substantially unitary article, having an air inlet port, a transducer port, and two cuff ports, whereby the device may service either a high volume, sometimes called adult, or low volume, sometimes called infant, blood pressure cuff. While the blood pressure cuff to be used is coupled to the appropriate cuff port, the other cuff port is used to sample ambient pressure, thereby zeroing the system before it takes a measurement.

The manifold further includes four valve seats, two for receiving a high- and low-pressure distribution valve, respectively, and two for receiving a high- and low-pressure relief valve, respectively. The high- and low-pressure distribution valves, which control the flow of air to the first and second cuff ports, respectively, both utilize a solenoid, and therefore have two positions, namely, energized and de-energized. In the energized position, each distribution valve allows its corresponding cuff port to communicate with a first plenum chamber, the first plenum chamber being in communication with an air pump through the air inlet port. In the de-energized position, each distribution valve allows its corresponding cuff port to communicate with the atmosphere, and seals off communication between the cuff port and the first plenum chamber.

A transducer for measuring the pressure in a blood pressure cuff and the corresponding amplitude of oscillometric pulses caused by the flow of blood through the brachial artery is mounted on and electrically connected to a circuit board. The manifold is mounted on the circuit board such that it is in communication with the transducer through the transducer port of the manifold.

A blood pressure measurement is taken by zeroing the system and energizing the distribution valve corresponding to the active cuff port, namely, the cuff port to which the blood pressure cuff is coupled, thereby allowing the active cuff port to communicate with the first plenum chamber.

Using conventional electronic timing and control circuits, the air pump is energized, thereby causing pressurized air to pass through the air inlet port into the first plenum chamber of the manifold, and through the active cuff port, thereby inflating the blood pressure cuff to a predetermined pressure. The pump is then de-energized, after which the transducer measures the pressure in the blood pressure cuff and any corresponding oscillometric pulses. The distribution valve corresponding to the active cuff port is then de-energized for a predetermined period of time, thereby allowing the blood pressure cuff to vent to atmosphere. A sequence of bleeding the blood pressure cuff for a predetermined period of time and measuring the pressure and amplitude of the corresponding oscillometric pulses is continued until both systolic and diastolic pressures are measured. The blood pressure cuff is then vented completely.

As noted above, the manifold also provides valve seats for receiving high- and low-pressure relief valves. The relief valves actuate only in an emergency situation arising when the pressure in the manifold exceeds a preset limit.

DETAILED DESCRIPTION OF THE INVENTION

Figure 1:
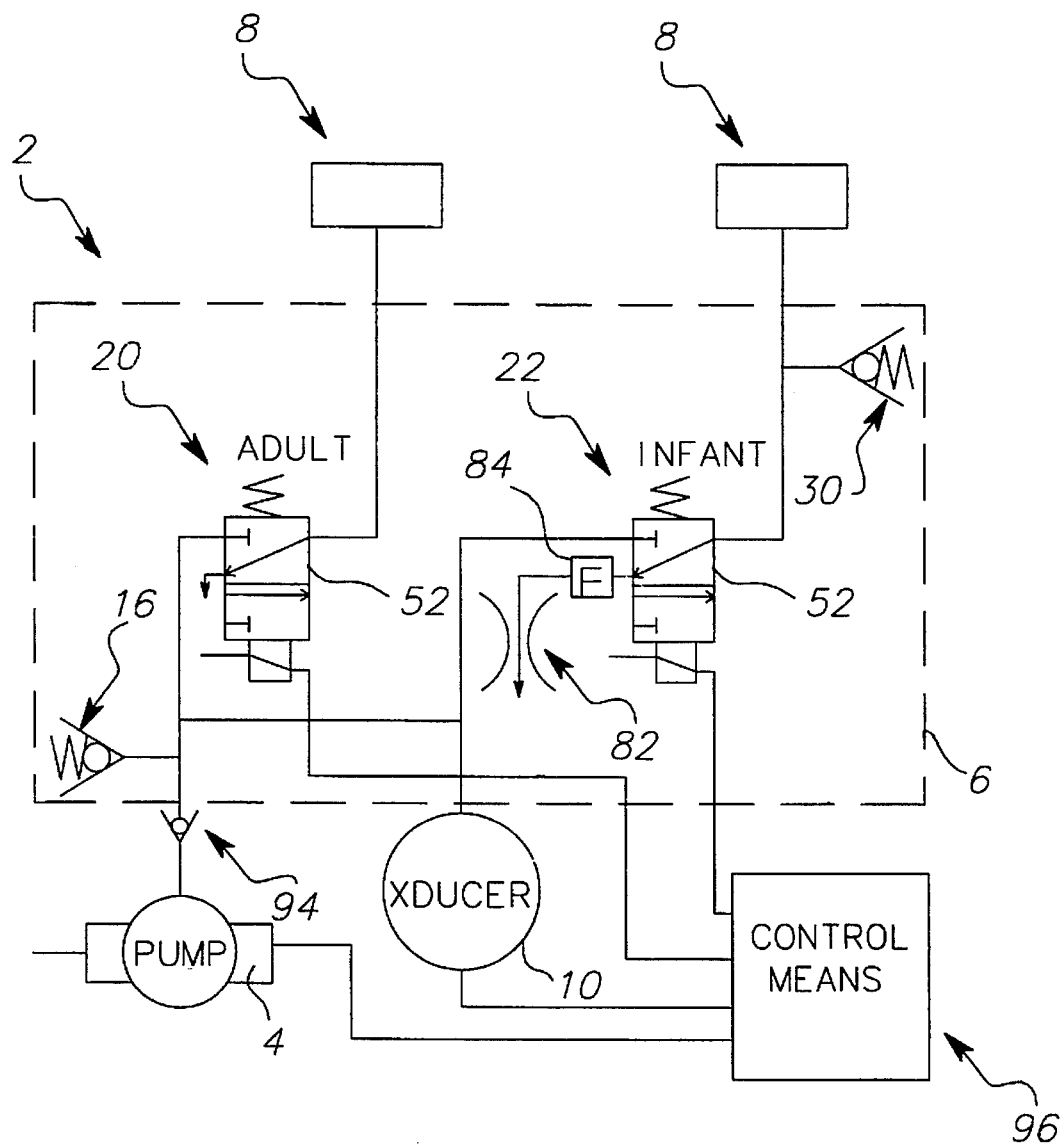
FIG. 1 is a schematic of a blood pressure monitoring device utilizing the manifold of FIG. 2.

As shown in FIG. 1, the blood pressure monitoring device 2 has an air pump 4 which generates pressurized air when energized, a pressure transducer 10 for measuring the pressure and amplitude of oscillometric pulses in the blood pressure cuff 8, and a manifold 6 which connects and serves as an integral part of the components of the blood pressure monitoring device 2. The blood pressure monitoring device 2 utilizes control means 96 for energizing and de-energizing the air pump 4 and distribution and relief valves, as will be discussed below.

Figure 2:
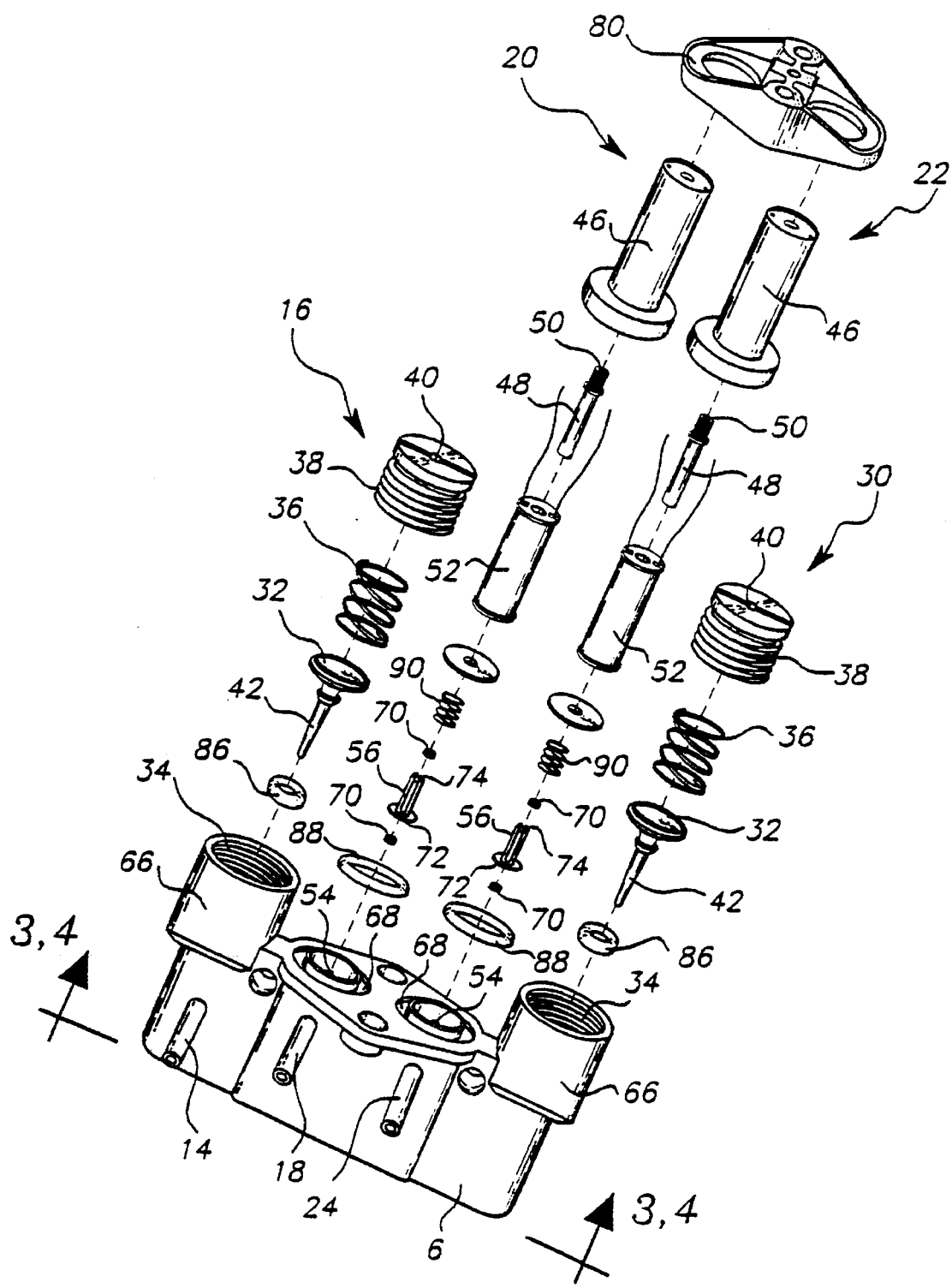
FIG. 2 is an exploded isometric view of a manifold for use in a blood pressure monitoring device.

As illustrated in FIG. 2, the manifold 6 is an integrally formed, substantially unitary structure, which may be made, for example, by injection molding. All of the ports and valve seam, as will be described below, are an integral pan of the manifold 6, thereby eliminating the need for intermediate hoses and clamps and thereby minimizing the inadvertent leakage of air from the blood pressure monitoring device 2. Utilizing such a unitary, structure further serves to reduce the stress on the valves, thereby increasing the longevity of the device, and to reduce the size and cost of the blood pressure monitoring device.

The manifold 6 has an air inlet port 14 to communicate with the air pump 4, a first cuff port 18 and a second cuff port 24, such that a blood pressure cuff 8 may be coupled to either the first cuff port 18 or the second cuff port 24. For example, in the embodiment illustrated in FIGS. 2 through 4, either an adult blood pressure cuff is coupled to the first cuff port 18 or an infant blood pressure cuff is coupled to the second cuff port 24, depending on the age of the patient whose blood pressure is being monitored. If an adult cuff is coupled to the first cuff port 18, the blood pressure monitoring device 2 samples ambient pressure through the second cuff port 24 at the beginning of a measurement to zero the system. Similarly, if an infant cuff is coupled to the second cuff port 24, the first cuff port 18 will be used to sample ambient pressure. It will be appreciated by one of ordinary skill in the art that the manifold 6 may be made to service only a single blood pressure cuff, as long as the system has some means for sampling ambient pressure to zero the system.

The integral structure of the manifold 6 further includes two relief valve seats 66 adapted to receive a high-pressure relief valve 16 and a low-pressure relief valve 30, respectively, and two distribution valve seats 68 adapted to receive a high-pressure distribution valve 20 and a low-pressure distribution valve 22, respectively, the high- and low-pressure distribution valves 20 and 22 being mounted to the manifold by a yoke 80.

Figure 3:
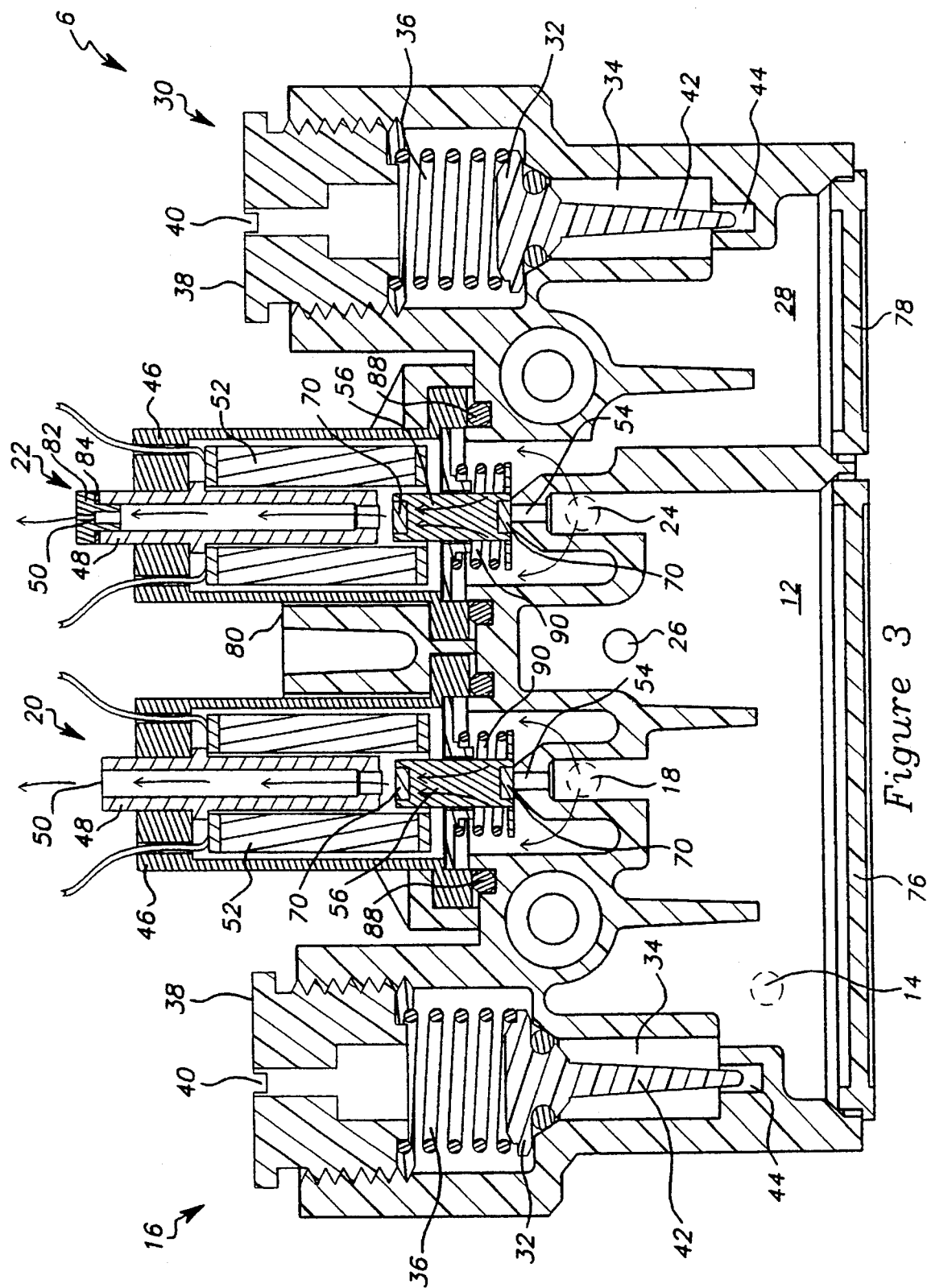
FIG. 3 is a cross-sectional plan view taken on line 3—3 of FIG. 2, showing the solenoids in a de-energized position.
Figure 4:
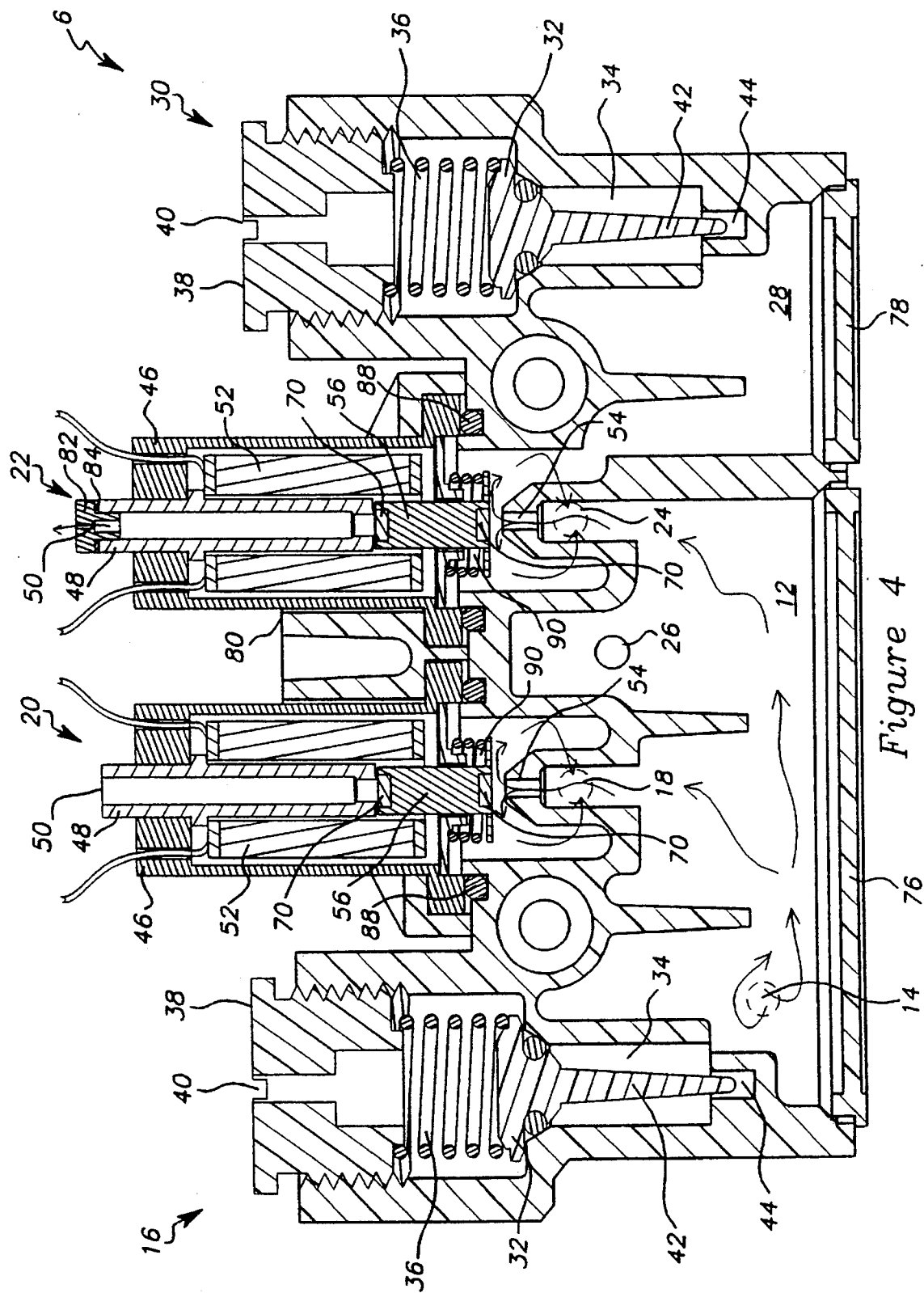
FIG. 4 is a cross-sectional plan view taken on line 4—4 of FIG. 2, showing the solenoids in an energized position.

As best seen in FIGS. 3 and 4, the manifold 6 has a first plenum chamber 12 and a second plenum chamber 28. The first plenum chamber 12 is substantially closed from the atmosphere by cap 76 while the second plenum chamber 28 is substantially closed from the atmosphere by cap 78. The first plenum chamber 12 is in communication with the high-pressure relief valve 16, the air pump 4 through the air inlet port 14, the pressure transducer 10 through the transducer port 26, and selectively with the first and second cuff ports 18 and 24, as determined by the high-pressure distribution valve 20 and the low-pressure distribution valve 22, respectively, as will be discussed in greater detail below. The second plenum chamber, as illustrated in FIGS. 3 and 4, communicates with the low-pressure relief valve 30, the second cuff port 24, and selectively with the first plenum chamber 12, as determined by the low-pressure distribution valve 22, as will be discussed in greater detail below.

As illustrated in FIGS. 2 through 4, the high-pressure relief valve 16 and the low-pressure relief valve 30 each comprises a piston 32 having a stylus 42 which is fitted with an o-ring 86, typically made of rubber. The piston 32 and o-ring 86 are seated in cortical bore 34 by a compression spring 36 and a plug 38, the plug 38 being adapted to allow air to pass through it from the manifold 6 to atmosphere, for example, as illustrated in FIG. 2, by having a cylindrical opening 40. As shown in FIG. 3, the plug 38 may be threaded, thereby being adjustable. As will be understood by one of ordinary skill in the ark the mount of force applied to the piston 32 by the compression spring 36 governs the pressure at which the piston 32 will become unseated, thereby allowing air to pass from the manifold 6 to atmosphere through the opening 40 of plug 38.

The use of a conical bore 34 in each of the relief valve seats 66 is beneficial because it allows the piston 32 and o-ring 86 to fit tightly in the conical bore 34 when the piston 32 is seated, such that when the relief pressure, which is governed by the compression spring 36 as noted above, is reached, the piston 32 becomes unseated, or "pops open," suddenly. This action relieves the pressure in the manifold 6 quickly, unlike a cylindrical bore and flat seat design which would act as a slow leak. This is advantageous because it is important to relieve the pressure as quickly as possible, in order to minimize discomfort and risk of injury to the patient whose blood pressure is being monitored.

As illustrated in FIGS. 3 and 4, the correct alignment of each piston 32 in its respective relief valve seat 66 is controlled by the stylus 42 of each piston 32. Each stylus 42 sits in its respective clearance opening 44 in manifold 6, the length and size of the stylus 42 being such to provide adequate alignment of the piston 32 while having sufficient clearance between the stylus 42 and the manifold 6 to reduce the drag on the stylus 42 as it moves to relieve the pressure in the manifold 6. Use of such a design is advantageous in that it reduces undesirable drag which occurs in alignment schemes using tight-fitting shafts and sleeves.

As illustrated in FIGS. 2 through 4, the high-pressure distribution valve 20 and the low-pressure distribution valve 22 each comprises a sleeve 46, a cylindrical, stationary core 48 mounted axially in the sleeve 46, a solenoid coil 52, a compression spring 90 and a moving core 56. Each sleeve 46 is sealed in its respective distribution valve seat 68 by an o-ring 88, the moving core 56 and the stationary core 48 of each distribution valve being axially aligned with a corresponding solenoid port 54 in the manifold 6.

As further illustrated in FIGS. 2 through 4, each moving core 56 has a sealing surface 70 on its first end 72 and on its second end 74. The sealing surface may be made of rubber or any other suitable material.

As best seen in FIG. 3, when either of the solenoid coils 52 is de-energized, the sealing surface 70 on the first end 72 of the moving core 56 is forced against the solenoid port 54 by the compression spring 90, thereby preventing the passage of air from the first plenum chamber 12 through the cuff port corresponding to the respective distribution valves. For example, de-energizing the solenoid coil 52 in the high-pressure distribution valve 20 will cause the moving core 56 to seal off the communication between the first plenum chamber 12 and the first cuff port 18. Similarly, de-energizing the solenoid coil 52 in the low-pressure distribution valve 22 will cause the corresponding moving core 56 to seal off communication between the first plenum chamber 12 and the second cuff port 24.

Correspondingly, de-energizing the solenoid coils 52 allows the first cuff port 18 and second cuff port 24 to communicate with the atmosphere via the cylindrical passageway 50 in stationary core 48 of their corresponding distribution valves, 20 and 22, respectively. Thus, de-energizing the coils 52 vents the respective cuff ports 18 and 24 to atmosphere to gradually decrease the pressure in the cuff.

Use of such a design is advantageous, in that the sleeve 46 in each of the distribution valves 20 and 22 acts as a magnetic return path for the moving core 56, as well as an air-tight section of the air-flow path between the cuff ports 18 and 24, and the atmosphere.

In contrast, as illustrated in FIG. 4, when either of the solenoid coils 52 is energized, the corresponding moving core 56 is drawn into the solenoid coil 52 such that the sealing surface 70 on the second end 74 of the moving core 56 is forced against the stationary core 48, thereby preventing the passage of air from the manifold 6 through the cylindrical passageway 50 of the stationary core 48 to atmosphere.

Correspondingly, energizing the solenoid coils 52 in the high- and low-pressure distribution valves 20 and 22 allows the first plenum chamber 12 to communicate with the first and second cuff ports, 18 and 24, respectively. Under these circumstances, the pressure in the plenum chamber 12 equalizes to the pressure of the first and second cuff ports 18 and 24.

Figure 5:
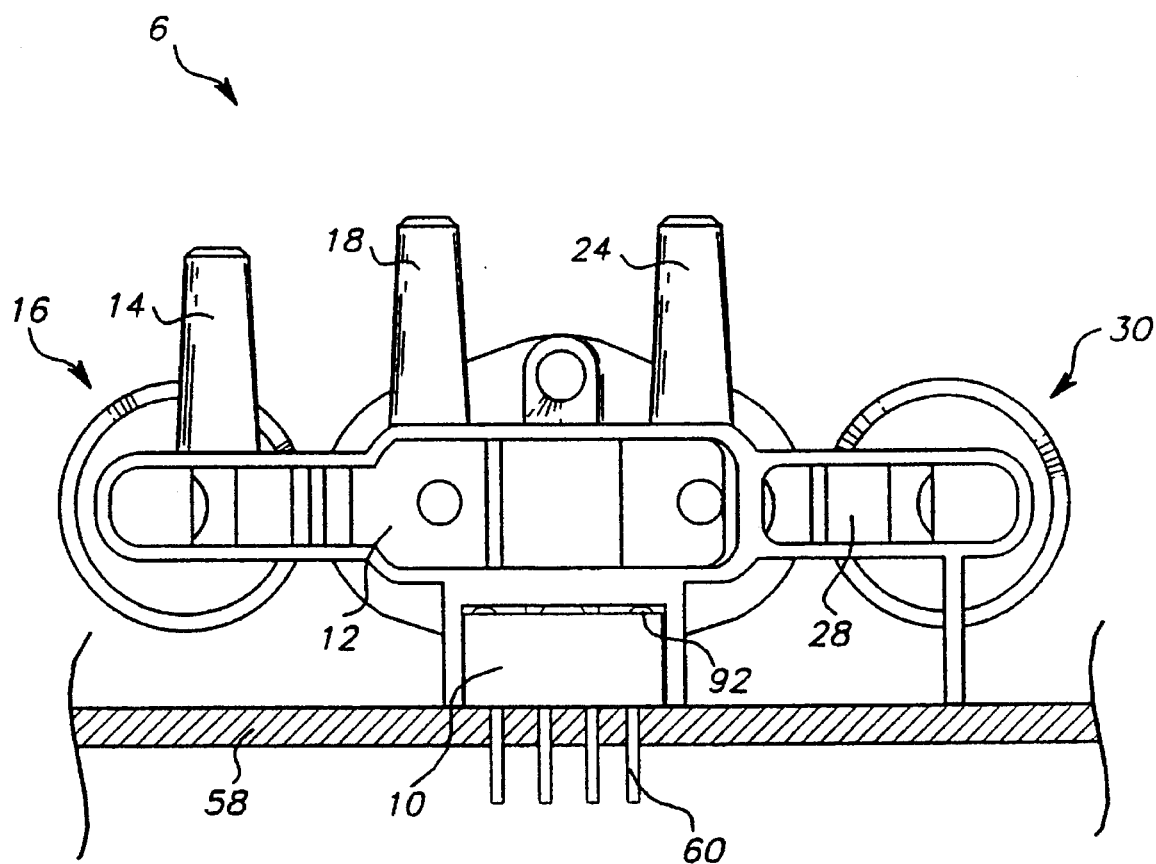
FIG. 5 is a front plan view of the blood pressure monitoring device of FIG. 2.

As illustrated in FIG. 5, the pressure transducer 10 is mounted on, and electrically connected by leads 60 to, circuit board 58. The manifold 6 is mounted on the circuit board 58 such that the transducer port 26, as illustrated in FIGS. 3 and 4, communicates with a pressure port, not shown, of the pressure transducer 10, such that the pressure transducer 10 measures the pressure and amplitude of oscillometric pulses in the blood pressure cuff 8 coupled to the manifold 6, via the first plenum chamber 12. An o-ring seal 92 is mounted between the manifold 6 and pressure transducer 10, thereby sealing the transducer 10 to the manifold 6.

As discussed previously, a blood pressure cuff 8 may be coupled to either the first cuff port 18 or the second cuff port 24 of manifold 6. The blood pressure monitoring device 2 therefore has two modes, namely, high-pressure, for inflating an adult cuff, and low-pressure, for inflating an infant cuff.

Referring to FIGS. 3 and 4, when operating in the high-pressure mode, such that the blood pressure cuff 8 is a relatively high-volume cuff and is coupled to the first cuff port 18, the solenoid coil 52 in the low-pressure distribution valve 22 is energized, thereby allowing the pressure transducer 10 to sample ambient pressure through the second cuff port 24 to zero the system. The solenoid coil 52 in the low-pressure distribution valve 22 is then de-energized, and the solenoid coil 52 in the high-pressure distribution valve 20 is energized, thereby allowing communication between the air pump 4 coupled to the manifold 6 through the air inlet port 14 and the blood pressure cuff 8 coupled to the manifold 6 via the first cuff port 18. The air pump 4 is then energized, causing pressurized air to pass through the air inlet port 14 into the first plenum chamber 12 and through the first cuff port 18 to inflate the blood pressure cuff 8 to a predetermined pressure, typically 30 mmHg above the expected systolic blood pressure, as measured by the pressure transducer 10. The pressure transducer 10 concurrently checks for the presence of oscillometric pulses in the cuff indicating a pressure below systole and, if necessary, the pressure is increased further until a pressure above systole is reached.

After a predetermined pressure above systole is reached, the air pump 4 is de-energized. A check valve 94, prevents air from bleeding back through the air pump. After the pressure and amplitude of oscillometric pulses in the cuff are measured and recorded, the solenoid coil 52 in the high-pressure distribution valve 20 is de-energized for a predetermined period of time, thereby allowing air to vent from the blood pressure cuff 8 through the first cuff port 18 and through the cylindrical passageway 50 in the stationary core 48 to atmosphere. After the high-pressure valve 20 is once again energized to couple the first cuff port 18 to the first plenum chamber 12, the pressure and amplitude of oscillometric pulses are measured through the transducer port 26 and recorded. A sequence of pressure bleeding by de-energizing the solenoid coil 52 for a predetermined period of time, re-energizing the solenoid coil 52, and taking pressure and amplitude measurements via the pressure transducer 10 continues until both systolic and diastolic pressures are detected. After systolic and diastolic pressures are detected, as determined by an empirical formula, the solenoid coil 52 in the high-pressure distribution valve 20 is de-energized to completely vent the blood pressure cuff 8 to atmosphere. If the electronic circuitry malfunctions, such that the solenoid coil 52 is stuck in an energized position, the solenoid coil 52 in the low-pressure distribution valve 22 would also be energized, thereby venting the blood pressure cuff 8 through the second cuff port 24, the two cuff ports being in communication via the first plenum chamber 12.

Similarly, when operating in the low-pressure mode, such that the blood-pressure cuff 8 is an infant blood pressure cuff and is coupled to the second cuff port 24, the solenoid coil 52 in the high-pressure distribution valve 20 is energized, thereby allowing the pressure transducer 10 to sample ambient pressure through the first cuff port 18, to zero the system. The solenoid coil 52 in the high-pressure distribution valve 20 is then de-energized, and the solenoid coil 52 in the low-pressure distribution valve 22 and the air pump 14 are energized, such that pressurized air generated by the air pump 4 inflates the blood pressure cuff 8 after passing through the first plenum chamber 12 and second cuff pen 24. After the blood pressure cuff 8 is inflated to a predetermined pressure, as measured by the pressure transducer 10, the control means 96, for example a microprocessor, initiates a sequence of pressure-bleeding and measurement-taking of pressure and amplitude of oscillometric pulses, similar to that described above for the high-pressure mode.

Given that the volume of the infant blood pressure cuff is relatively low, the rate at which the air pump 4 inflates the infant cuff is reduced, as compared to the rate of inflation for the adult cuff. In addition, a flow restrictor 82 and filter 84 are installed over the cylindrical passageway 50 of the low-pressure distribution valve 22, to slow the rate at which air escapes from the infant blood pressure cuff, thereby allowing more precise control of the bleed step.

After both systolic and diastolic pressures are detected, as determined by the control means 96, the solenoid coils 52 in the high-pressure and low-pressure distribution valves 20 and 22 are both energized, such that the final bleed to deflate the blood pressure cuff 8 is through the first cuff port 18. This is quicker, and therefore more advantageous, given the flow restrictor 82 on the low-pressure distribution valve 22.

To ensure the safety of the patient having his blood pressure monitored, the high-pressure relief valve 16 and the low-pressure relief valve 30 are set to relieve the pressure in the manifold if it exceeds a preset limit for a high-volume blood pressure cuff or a low-volume blood pressure cuff, respectively, whichever is in use at any given time.

More specifically, when operating in the high-pressure mode, the high-pressure relief valve 16 will actuate when the pressure in the manifold, and therefore in the cuff, exceeds a predetermined value. For example, if operation in a high-pressure mode is typically in the range of 80–290 mmHg, the high-pressure relief valve 16 is set to actuate if the pressure reaches or exceeds 310 mmHg.

Similarly, when operating in the low-pressure mode, the low-pressure relief valve 30 will actuate to relieve the pressure in the manifold 6, and therefore the blood pressure cuff 8, when the pressure exceeds a preset value. For example, if operation in the low-pressure mode is typically in the range of 40–170 mmHg, the low-pressure relief valve 30 will be set to actuate if the pressure reaches or exceeds 200 mmHg. It will be understood by one of ordinary skill in the art that the pressure at which the relief valves 16 and 30 actuate is adjustable, and the above values are given only as examples.

A blood pressure monitoring device utilizing an integrally formed, substantially unitary manifold has been shown and described. From the foregoing, it will be appreciated that, although embodiments of the invention have been described herein for purposes of illustration, various modifications may be made without deviating from the spirit and scope of the invention.

We claim:

1. A blood pressure monitoring device comprising:
   an air pump;
   a manifold coupled to the air pump;
   a blood pressure cuff coupled to the manifold;
   a pressure transducer coupled to the manifold; and
   wherein the manifold is provided with a first cuff port; a second cuff port; a first plenum chamber; a first distribution valve integrally seated in the manifold, the first distribution valve being in communication with the first plenum chamber and with the blood pressure cuff and with atmosphere, whereby the distribution valve selectively allows the blood pressure cuff to communicate with the first plenum chamber and with the atmosphere; a second distribution valve wherein the first distribution valve is a high-pressure distribution valve and the second distribution valve is a low-pressure distribution valve; the first plenum chamber having an air inlet port communicating with the air pump, a high-pressure relief valve seated in the manifold, the high-pressure distribution valve selectively allowing the first plenum chamber to communicate with the first cuff port, the low-pressure distribution valve selectively allowing the first plenum chamber to communicate with the second cuff port so that the blood pressure cuff can be coupled to either the first or the second cuff port to selectively communicate with the first plenum chamber, and a transducer port communicating with the pressure transducer; and a second plenum chamber communicating with the second cuff port, the second plenum chamber having a low-pressure relief valve, the low-pressure distribution valve selectively allowing the second plenum chamber to communicate with the first plenum chamber.

2. The device according to claim 1 wherein the high-pressure relief valve and the low-pressure relief valve each further comprises:
   a piston seated in a conical bore by a compression spring and a plug, the plug including means for allowing air to pass through the plug, the piston being aligned in the conical bore by a stylus that fits loosely through a clearance opening in the manifold.

3. The device according to claim 1 wherein the high-pressure distribution valve and the low-pressure distribution valve each further comprises:
   a sleeve coupled to the manifold;
   a stationary, core mounted axially in the sleeve, the stationary core including means for allowing air to pass through it;
   a solenoid coupled to the sleeve such that the stationary core extends into the solenoid;
   a solenoid port in the manifold which communicates with the first plenum chamber; and
   a moving core which substantially creates a seal with the stationary core when the solenoid is energized, and which substantially creates a seal with the solenoid port in the manifold when the solenoid is de-energized.

4. The device according to claim 1 wherein the blood pressure cuff is a relatively high-volume blood pressure cuff.

5. The device according to claim 1 wherein the blood pressure cuff is a relatively low-volume blood pressure cuff.

6. A blood pressure monitoring device comprising:
   an air pump;
   a manifold coupled to the air pump, wherein the manifold is provided with a first plenum chamber;
   a blood pressure cuff coupled to the manifold;
   a first distribution valve integrally seated in the manifold, the first distribution valve being in communication with the first plenum chamber and with the blood pressure cuff and with atmosphere, whereby the distribution valve selectively allows the blood pressure cuff to communicate with the first plenum chamber and with the atmosphere; and a pressure transducer coupled to the manifold, wherein the pressure transducer is mounted on and electrically connected to a circuit board, the manifold is mounted on the circuit board to overlie the pressure transducer, and the manifold includes a transducer port communicating with the pressure transducer.

7. A blood pressure monitoring device having an air pump that generates pressurized air when energized, a blood pressure cuff coupled to the air pump and a pressure transducer coupled to the blood pressure cuff, further comprising:

an integrally formed, substantially unitary manifold having an air inlet port in communication with the air pump; a transducer port in communication with the pressure transducer; a first cuff port in communication with the blood pressure cuff; a first relief valve seat and a second relief valve seat wherein the first relief valve seat engages a high-pressure relief valve and the second relief valve seat engages a low-pressure relief valve, the high-pressure relief valve and the low-pressure relief valve each further comprising a piston seated in a conical bore by a compression spring and a plug, the plug including means for allowing air to pass through the plug, the piston being aligned in the conical bore by a stylus that fits loosely through a clearance opening in the manifold; a first distribution valve seat and a second distribution valve seat wherein the first distribution valve seat engages a high-pressure distribution valve and the second distribution valve seat engages a low-pressure distribution valve; a first plenum chamber in communication with the air inlet port, the high-pressure relief valve seat, and both the high-pressure and low-pressure distribution valve seats; a second plenum chamber in communication with the low-pressure distribution valve seat and the low-pressure relief valve seat; and means for sampling ambient pressure.

8. The device according to claim 7 wherein the high-pressure distribution valve and the low-pressure distribution valve each further comprises:

a sleeve coupled to the manifold;

a stationary core mounted axially in the sleeve, the stationary core including means for allowing air to pass through it;

a solenoid coupled to the sleeve such that the stationary core extends into the solenoid;

a solenoid port in the manifold which communicates with the first plenum chamber; and a moving core which substantially creates a seal with the stationary core when the solenoid is energized, and which substantially creates a seal with the solenoid port in the manifold when the solenoid is de-energized, thereby selectively allowing the first plenum chamber to communicate with the first cuff port.

9. The device according to claim 8 wherein the moving core has a sealing surface on a first end and on a second end such that when the solenoid is energized, the moving core is drawn into the solenoid and creates a seal between the first end of the moving core and the stationary core, thereby preventing air from escaping from the manifold to atmosphere, and such that when the solenoid is de-energized, the moving core creates a seal between the second end of the moving core and the solenoid port in the manifold, thereby preventing air from passing from the first plenum chamber to the blood pressure cuff and thereby allowing air from the blood pressure cuff to vent to the atmosphere through the stationary core.

10. The device according to claim 8, further comprising:

control means for energizing and de-energizing the air pump, the solenoid in the high-pressure distribution valve and the solenoid in the low-pressure distribution valve, coupled to the manifold.

11. The device according to claim 10 further comprising a second cuff port and wherein the high-pressure distribution valve is coupled to the first cuff port and the low-pressure distribution valve is coupled to the second cuff port.

12. The device according to claim 11 wherein the control means energizes the solenoid in the high-pressure distribution valve, causing the moving core to prevent air from passing from the manifold to the atmosphere through the stationary core, and energizes the air pump, causing the air pump to generate pressurized air which passes through the air inlet port into the first plenum chamber where it passes through the first cuff port into the blood pressure cuff, thereby inflating the blood pressure cuff to a predetermined pressure as measured by the transducer, the control means de-energizing the pump when the predetermined pressure is reached, the transducer measuring the pressure and the amplitude of oscillometric pulses in the blood pressure cuff, the control means de-energizing the solenoid in the high-pressure distribution valve for a predetermined period of time, thereby preventing air from passing from the first plenum chamber to the blood pressure cuff and allowing air to vent from the blood pressure cuff to the atmosphere, the transducer taking a second pressure and amplitude measurement, a sequence of pressure bleeding by de-energizing the solenoid for a predetermined period of time and taking pressure and amplitude measurements continuing until both systolic and diastolic pressures are measured, the control means then de-energizing the solenoid to completely vent the blood pressure cuff, the high-pressure relief valve actuating only in an emergency situation arising when the pressure in the manifold exceeds a preset limit.

13. The device according to claim 11 wherein the control means energizes the solenoid in the low-pressure distribution valve causing the moving core to prevent air from passing from the manifold to the atmosphere through the stationary core, and energizes the air pump, causing the air pump to generate pressurized air which passes through the air inlet port into the first plenum chamber where it passes through the second cuff port into a second blood pressure cuff, thereby inflating the second blood pressure cuff to a predetermined pressure as measured by the transducer, the control means de-energizing the pump when the predetermined pressure is reached, the transducer measuring the pressure and the amplitude of oscillometric pulses in the second blood pressure cuff, the control means de-energizing the solenoid in the tow-pressure distribution valve for a predetermined period of time, thereby preventing air from passing from the first plenum chamber to the second blood pressure cuff and allowing air to vent from the second blood pressure cuff to the atmosphere, the transducer then taking a second pressure and amplitude measurement, a sequence of pressure bleeding by de-energizing the solenoid for a predetermined period of time and taking pressure and amplitude measurements continuing until both systolic and diastolic pressures are measured, the control means energizing both the solenoid in the high-pressure distribution valve and the solenoid in the low-pressure distribution valve, thereby completely venting the second blood pressure cuff through the first cuff port, the low-pressure relief valve actuating only in an emergency situation arising when the pressure in the manifold exceeds a preset limit.

14. The device according to claim 13 wherein a flow restrictor is coupled to the low-pressure distribution valve, thereby decreasing the rate at which air vents from the second blood pressure cuff to the atmosphere.

15. A blood pressure monitoring device comprising:

an air pump;

a manifold coupled to the air pump;

a blood pressure cuff coupled to the manifold;

a distribution valve integrally seated in the manifold wherein the distribution valve selectively allows the air pump to communicate with the blood pressure cuff; and a pressure transducer coupled to the manifold, wherein the pressure transducer is mounted on and electrically connected to a circuit board, the manifold is mounted on the circuit board to overlie the pressure transducer, and the manifold includes a transducer port communicating with the pressure transducer.

16. A blood pressure monitoring device comprising:

an air pump;

a manifold coupled to the air pump;

a blood pressure cuff coupled to the manifold such that the air pump communicates with the blood pressure cuff;

a pressure transducer coupled to the manifold; and wherein the manifold further comprises a first cuff port, a second cuff port, a first plenum chamber having an air inlet port communicating with the air pump, a high-pressure relief valve, a high-pressure distribution valve selectively allowing the first plenum chamber to communicate with the first cuff port, a low-pressure distribution valve selectively allowing the first plenum chamber to communicate with the second cuff port so that the blood pressure cuff can be coupled to either the first or the second cuff port to selectively communicate with the first plenum chamber, a transducer port communicating with the pressure transducer, and a second plenum chamber communicating with the second cuff port, the second plenum chamber having a low-pressure relief valve, the low-pressure distribution valve selectively allowing the second plenum chamber to communicate with the first plenum chamber.

17. A manifold for use in a blood pressure monitoring device having an air pump that generates pressurized air when energized, a blood pressure cuff coupled to the air pump and a pressure transducer coupled to the blood pressure cuff, comprising:

an integrally formed, substantially unitary structure having an air inlet port adapted to communicate with the air pump; a transducer port adapted to communicate with the pressure transducer; a first cuff port adapted to communicate with the blood pressure cuff; a first relief valve seat and a second relief valve seat wherein the first relief valve seat is adapted to receive a high-pressure relief valve and the second relief valve seat is adapted to receive a low-pressure relief valve; a first distribution valve seat and a second distribution valve seat wherein the first distribution valve seat is adapted to receive a high-pressure distribution valve and the second distribution valve seat is adapted to receive a low-pressure distribution valve; a first plenum chamber adapted to communicate with the air inlet port, the high-pressure relief valve seat, and both the high-pressure and low-pressure distribution valve seats; a second plenum chamber adapted to communicate with the low-pressure distribution valve seat and the low-pressure relief valve seat; and means for sampling ambient pressure.

* * * * *

UNITED STATES PATENT AND TRADEMARK OFFICE
CERTIFICATE OF CORRECTION

PATENT NO. : 5,464,019
DATED : Nov. 7, 1995
INVENTOR(S) : R. Carver Anderson, et al It is certified that error appears in the above-indentified patent and that said Letters Patent is hereby corrected as shown below:

In column 8, claim 3, line 40, after "stationary" and before "core", please delete ",".

In column 10, claim 13, line 50, please delete "tow-pressure" and insert therefor --low-pressure--.

Signed and Sealed this

Twenty-sixth Day of March, 1996

Attest:

BRUCE LEHMAN

Attesting Officer       Commissioner of Patents and Trademarks